United States Patent [19]

Iwai et al.

[11] Patent Number: 5,334,294
[45] Date of Patent: Aug. 2, 1994

[54] METHOD OF CONTINUOUSLY PROCESSING WIRE MATERIAL AND DEVICE THEREFOR

[75] Inventors: Hirohisa Iwai, Yokohama; Kaisuke Shiroyama, Zama; Akira Matsuda; Takeo Nakamura, both of Nikko; Ryotomo Shirakawa, Imaichi, all of Japan

[73] Assignee: The Furokawa Electric Co., Ltd., Tokyo, Japan

[21] Appl. No.: 923,800
[22] PCT Filed: Jan. 16, 1991
[86] PCT No.: PCT/JP91/00027
 § 371 Date: Sep. 4, 1992
 § 102(e) Date: Sep. 4, 1992
[87] PCT Pub. No.: WO92/12819
 PCT Pub. Date: Aug. 6, 1992

[51] Int. Cl.$^5$ .............................. B23H 9/00
[52] U.S. Cl. ............ 204/129.55; 204/129.1; 204/129.75
[58] Field of Search .......... 204/129.1, 129.55, 129.75, 204/211

[56] References Cited

U.S. PATENT DOCUMENTS 2,605,218  7/1952  Gibbs et al. ............. 204/129.55
5,066,370  11/1991  Andreshak et al. ........ 204/129.1

FOREIGN PATENT DOCUMENTS 33-3857   5/1958  Japan .
53-104538 9/1978  Japan .
557386   11/1943  United Kingdom .

OTHER PUBLICATIONS

NTIS Tech Notes, Nov. 1986, J. L. Watkins, "Electrochemical Process Makes Fine Needles", p. 1218.

Primary Examiner—John Niebling
Assistant Examiner—Kishor Mayekar
Attorney, Agent, or Firm—Armstrong, Westerman, Hattori, McLeland & Naughton

[57] ABSTRACT

The present invention relates to a processing method of wire material and a processing device therefor at the times of intending to make the tip of wire materials such as guide wire for catheter thin and flexible by tapering.

When the wire material passes through the electrolytic tub, the wire speed is made constant and the current value is controlled, or the current value is made constant and the wire speed is controlled to give the processings such as tapering. For the electrolytic polishing bath, it is desirable to use a mixed bath comprising trivalent alcohol, perchloric acid and monovalent alcohol.

The inventive method exerts an effect that the tapering can be given efficiently and yet with high precision compared with the traditional method of mechanical polishing or the method of dipping one by one batchwise into the electrolytic polishing bath.

6 Claims, 4 Drawing Sheets

METHOD OF CONTINUOUSLY PROCESSING WIRE MATERIAL AND DEVICE THEREFOR

TECHNICAL FIELD

The present invention relates to a method of processing wire material and a processing device therefor at the times of intending to make the tip of wire materials such as guide wire for catheter thin and flexible by tapering, and the like.

BACKGROUND TECHNIQUES

For the guide wire for a catheter used for interposing into a human body, etc., it is required to be interposed easily making the tip portion of wire material thin and flexible by tapering. As an example, a portion of 100 to 200 mm at the tip of wire material of around 0.5 mm$\phi$ is tapered so that the diameter of the utmost tip portion is around 0.12 mm$\phi$ is used.

Traditionally, this tapering has been made first by mechanical polishing, but the mechanical polishing has a drawback of losing the superelasticity for the Ni-Ti superelastic alloy used usually as a guide wire for a catheter. Recently, therefore, an electrolytic polishing method by batch process is adopted, wherein the tip portion of a wire material is dipped, for example, into a polishing solution having a composition comprising 92% of $CH_3COOH$ and 8% of $HClO_4$, into a polishing solution having a composition comprising 20% of HF and 80% of $HNO_3$, or into a polishing solution having a composition comprising 60% of $H_2SO_4$, 30% of HF and 10% of glycerine.

This traditional electrolytic polishing method is however a method of polishing batch wise by dipping one by one into the electrolytic polishing bath while moving up and down manually. Hence, there arise the problems that the shape of the tapered portion varies widely and many workers are required, thus resulting in a high cost.

Moreover, traditional electrolytic polishing baths have the following problems. Namely, the acetic acid-perchloric acid bath has a strong bad smell and gives somewhat poor surface gloss after polishing, and the fluoric acid-nitric acid bath has a strong bad smell, gives poor surface gloss after polishing and requires high cost for effluent treatment to avoid a pollution problem. The sulfuric acid-fluoric acid-glycerine bath has no bad smell, but it gives poor surface gloss and requires high cost for effluent treatment.

DISCLOSURE OF THE INVENTION

The invention has been made as a result of diligent investigations to solve such problems and is concerned with a method of continuously processing wire material characterized in that, in the method of processing part of the wire material by electrolytic polishing, a long wire material is passed continuously through the electrolytic polishing bath with a cathode installed therein and electricity is turned on only when the processing portion passes through said electrolytic polishing bath.

Here, it is preferable from the point of efficiency that, when the nonprocessing portion passes through the electrolytic polishing bath, the wire speed is made high.

Further, the invention is concerned with a device for continuously processing wire material characterized in that an electrolytic tub having the same length as that of a processing portion of wire material, a wire material-advancing device for allowing the wire material to pass through the electrolytic tub, a cathode provided in the electrolytic tub, an anodic electricity-supply device for wire material and a power source generating device are equipped.

Here, as the shapes of processing portion, for example, tapered portion, grooved portion, etc. are intended, and, in order to make this tapered shape, grooved shape or the like arbitrarily variable the feeding speed of wire material-advancing device is desirable to be variable and the generating current of power source-generating device is also desirable to be variable.

Besides, as the composition of wire material, a superelastic alloy comprising 50.5 to 53.0 at % of Ni and the balance of Ti, or a superelastic alloy substituted part of Ni and/or Ti in 50.5 to 53.0 at % of Ni and 49.5 to 47.0 at % of Ti with any one kind or two or more kinds of Cr, Fe, Co, Mo, V, Pd, W and Cu within a range of 0.01 to 5.0 at % of each can be used.

Moreover, as the electrolytic polishing bath to be used for said continuously processing device, it is effective to use a bath comprising 10 to 50 vol. % of trivalent alcohol, 5 to 20 vol. % of perchloric acid and the balance of monovalent alcohol.

And, as the monovalent alcohol, ethanol or methanol is desirable and, as the trivalent alcohol, glycerine is desirable.

Besides, if the investigation is made from the aspects of installation, a bath of 80 to 95 vol. % acetic acid-20 to 5 vol. % perchloric acid can also be used.

In the following, the invention will be illustrated in more detail using diagrams.

As shown in FIG. 1, when tapering a wire material 1 while passing it through the electrolytic polishing bath, electricity is turned on between cathode 3 and electricity-supply roll 4 at the time of point A of wire material having reached the inlet of bath and said electricity is turned off at the time of point A having reached the outlet of bath (FIG. 2). By this procedure, the wire material is tapered in such a shape that the wire diameter increases gradually towards both ends making point A as a center as shown in FIG. 3. And, the length of the portion to be tapered AC is approximately equal to the length of electrolytic polishing bath AB (i.e. the length of wire material existed initially in the bath) and the distance between A and C and that between A and B are processed almost symmetrically. Besides, the diameter of point A becoming the minimum diameter of wire material is determined depending on the current to be turned on.

Moreover, by periodically turning on-off the current at a fixed period, a long processed material (FIG. 4) can be obtained. Hence, if cutting at point A and point A', tapered material at both ends is obtained and, if cutting at point A and point D, tapered material at one end is obtained.

The turning on-off of power source may be performed manually, but it goes without saying that it can be automated briefly by using a feedback circuit through the detection of winding length.

It is extremely effective from the point of cost reduction that, when passing the portion not to be tapered through the electrolytic polishing bath, the wire speed is made high, thus enhancing the productivity.

Further, the processing device will be illustrated in detail. FIG. 6 shows an outline diagram of the inventive device and FIG. 7 shows a partially magnified diagram. In FIG. 6 and FIG. 7, numeral 11 is a supply reel, numeral 12 is a wire material, numeral 13 is an anodic electricity-supply device (diagram shows electricity-supply roll), numeral 14 is an electrolytic tub, numeral 15 is an electrolytic polishing bath, numeral 16 is a cathode, numeral 17 is a wash tub, numeral 18 is a drying device, numeral 19 is a wire material-advancing device, numeral 20 is a power source-generating device, and numeral 21 is a winding reel, respectively.

The electrolytic polishing by the inventive device is performed, as shown in FIG. 7, in a way that electricity is supplied to anode by anodic electricity-supply device 13 provided outside the electrolytic tub, on the other hand, a cylindrical electrode formed so as to locate at both sides or to envelop the whole circumference of wire material securing a fixed distance from the wire material in electrolytic solution (i.e. electrolytic polishing bath) is provided to make this the cathode 16, and a variable fixed current is turned on by means of power source-generating device while allowing the wire material to run at a constant or variable appropriate speed by means of wire material-advancing device 19. Thereby, the tapering in an arbitrary shape can be achieved.

Since the tapering length is a contacting length of electrolytic solution with wire material, the length of the electrolytic tub is altered for fitting to the desired tapering length. For Controlling the shape of taper, it is only necessary to experimentally determine beforehand through the change in said feeding speed of wire material or the change in electrolytic current so that the desired shape can be achieved.

Next, the explanation will be made in detail about the electrolytic bath.

① Case of electrolytic polishing bath comprising perchloric acid-trivalent alcohol and monovalent alcohol The reason why perchloric acid was restricted to 5 to 20 vol. % is because, in the case of being under 5 vol. %, the stability of solution is damaged due to the consumption during electrolytic polishing. And, if being over 20 vol. %, safety becomes problematic and the surface gloss is damaged. Moreover, the reason why trivalent alcohol was restricted to 10 to 50 vol. % is because of that, in the case of being under 10 vol. %, the viscosity of both is low and the smoothness of surface is poor and, if being over 50 vol. %, the viscosity is too high resulting in difficult agitation of bath and generation of color unevenness.

As the monovalent alcohol, methanol or ethanol is excellent from the points of availability and viscosity.

As the trivalent alcohol, glycerine is excellent from the points of cost and availability.

② Case of electrolytic polishing bath comprising acetic acid and perchloric acid The reason why perchloric acid was restricted to 5 to 20 vol. % is because, in the case of being under 5 vol. %, the stability of solution is damaged due to the consumption in electrolytic polishing bath and, if being over 20 vol. %, the safety becomes problematic and the surface gloss is injured.

BEST EMBODIMENT TO PUT THE INVENTION INTO PRACTICE

For illustrating the invention in more detail, it will be described based on the following examples.

Example 1

Figure 1:
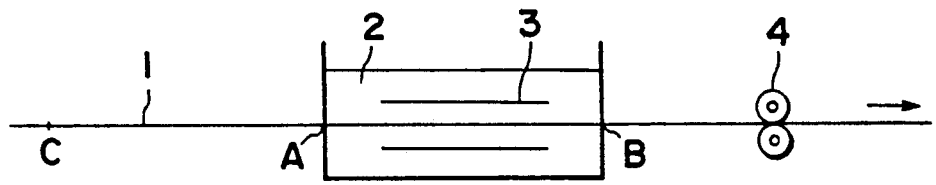
FIG. 1 shows one example of the inventive method and is a diagram illustrating the state at the time of electricity being turned on, FIG. 2 is a diagram illustrating the state at the time of electricity being turned off similarly.
Figure 2:
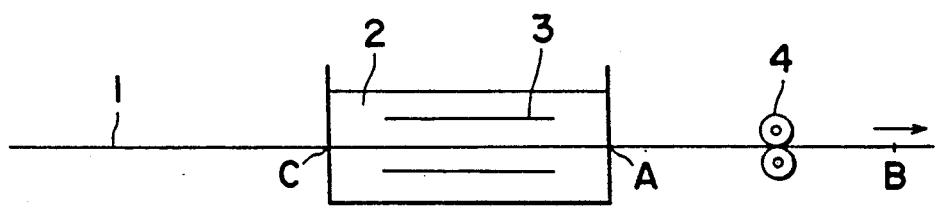
Figure 3:
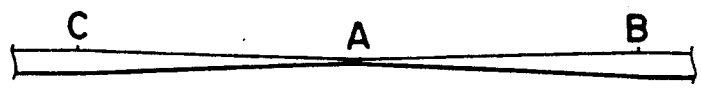
FIG. 3.
Figure 4:
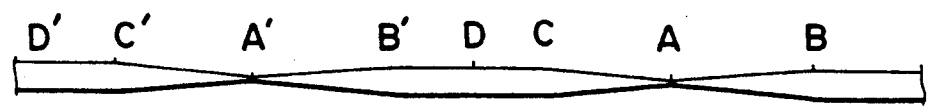
FIG. 4 are side views showing one example of wire material obtainable by the inventive method.

Using a 0.48 mmφ NiTi alloy wire (Ni:Ti=50 9:49.1 at %), the electrolytic polishing was conducted under following conditions:

| | |
|---|---|
| (1) Composition of electrolytic polishing bath | Ethanol 72% Glycerine 20% Perchloric acid 8% |
| (2) Bath temperature | 25° C.–30° C. |
| (3) Electrolytic tub | Length 125 mm |
| (4) Wire speed | Constant speed of 33 mm/min |
| (5) Total current turned on | 1.2 A |
| (6) On-off timing | According to FIG. 1 and FIG. 2 |

Figure 5:
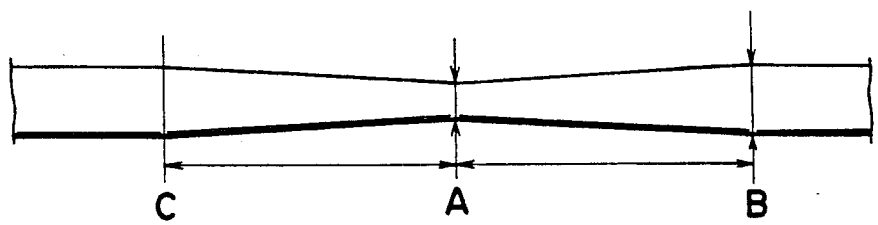
FIG. 5 is a side view showing the wire material obtained in Example 1 and 2 of the invention.

The shape of wire material thus obtained is shown in FIG. 5. As evident from FIG. 5, smooth tapering is given for the shape of taper obtained according to the invention.

Example 2

Using a 0.48 mmφ NiTi alloy wire (Ni:Ti=50.9:49.1 at %), the electrolytic polishing was conducted under following conditions:

| | |
|---|---|
| (1) Composition of electrolytic polishing bath | CH$_3$COOH 92% HClO$_4$ 8% |
| (2) Bath temperature | 25° C.–30° C. |
| (3) Electrolytic tub | Length 125 mm |
| (4) Wire speed | Constant speed of 33 mm/min |
| (5) Total current turned on | 1.2 A |
| (6) On-off timing | According to FIG. 1 and FIG. 2 |

The shape of wire material thus obtained is shown in FIG. 5. As evident from FIG. 5, smooth tapering is given to the tapered wire material obtained according to the invention.

Example 3

Figure 6:
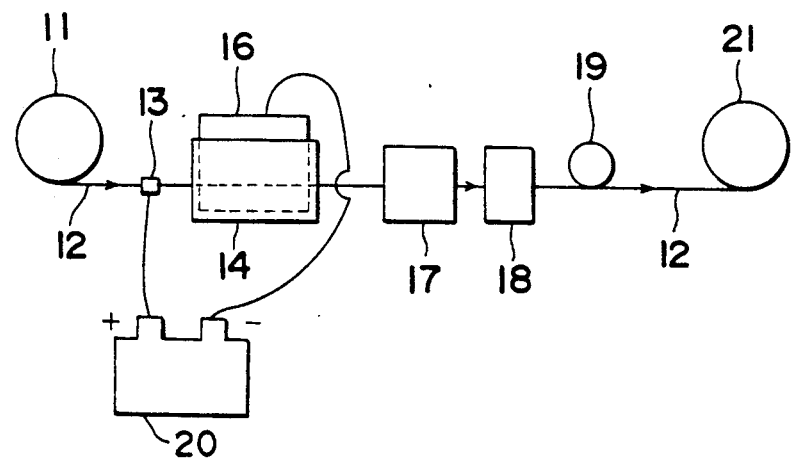
FIG. 6 is an outline diagram showing one example of the inventive device.
Figure 7:
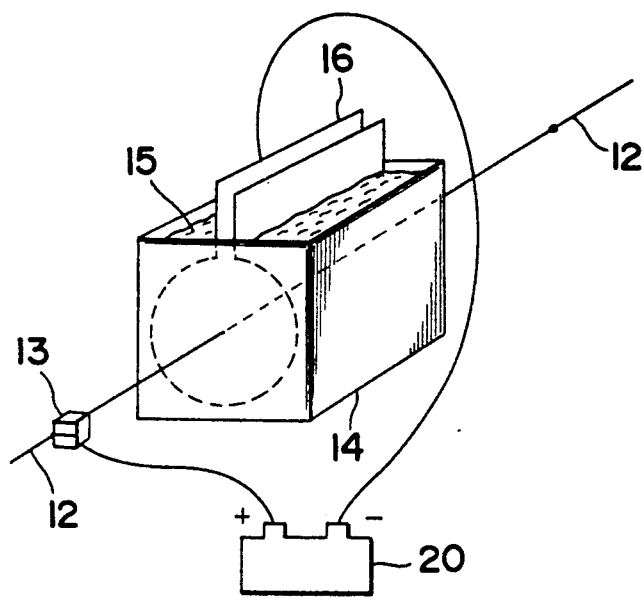
FIG. 7 is a partially magnified diagram of FIG. 6.

Employing a continuous tapering device shown in FIG. 6, the tapering of Ni-Ti alloy (Ni:Ti=50:50 at %) superelastic wire material was conducted.

Figure 8:
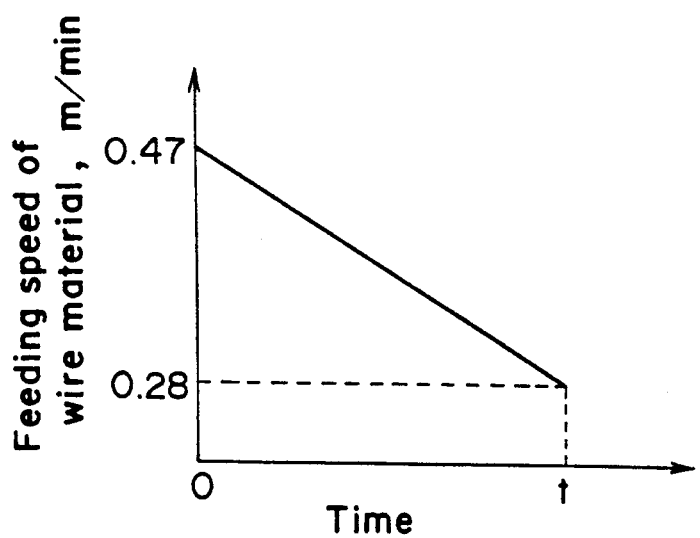
FIG. 8 is a chart showing the feeding speed of wire material used in Examples 3 and 5 of the invention.

Said 0.48 mmφ NiTi alloy wire material was wound around supply reel 11 and it was rewound around winding reel 21 changing the feeding speed of wire material by wire material-advancing device 19 as shown in FIG. 8. The turning-on of electricity was made by anodic electricity-supply device 13 and cathode 16. The electrolytic polishing conditions are as follows:

| | |
|---|---|
| (1) Composition of electrolytic polishing bath | Ethanol 72% Glycerine 20% Perchloric acid 8% |
| (2) Bath temperature | 25° C.-30° C. |
| (3) Electrolytic tub | Length 125 mm |
| (4) Wire speed | 0.28 m/min–0.47 m/min |
| (5) Total current turned on | 2A |

Figure 9:
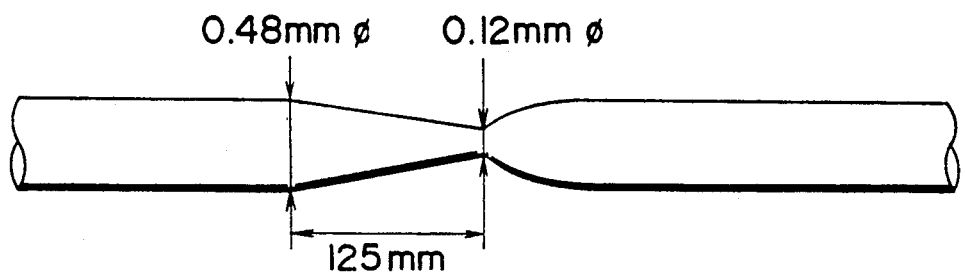
FIG. 9 is a side view showing the tapered wire material obtained in Example 3 and 5.

The shape of wire material thus obtained is shown in FIG. 9.

Example 4

Figure 10:
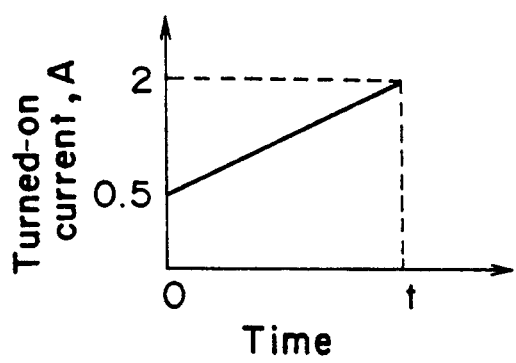
FIG. 10 is a chart showing the turned-on current used in Example 4 and 6.

Similarly to Example 3, however, making the feeding speed of wire material constant, the turned-on current was increased gradually as shown in FIG. 10.

The tapered wire material thus obtained was same as one shown in FIG. 9.

As evident from FIG. 9, smooth tapering is given to the tapered wire material obtained by the inventive device.

Example 5

Employing a continuous tapering device shown in FIG. 6, the tapering of Ni-Ti alloy (Ni:Ti=50.9:49.1 at %) super-elastic wire material was conducted.

Said 0.48 mmφ NiTi alloy wire material was wound around supply reel 11 and it was rewound around winding reel 21 changing the feeding speed of wire material by wire material-advancing device 19 as shown in FIG. 8. The turning-on of electricity was made by anodic electricity-supply device 13 and cathode 16. The electrolytic polishing conditions are as follows:

| | |
|---|---|
| (1) Composition of electrolytic polishing bath | $CH_3COOH$ 92% $HClO_4$ 8% |
| (2) Bath temperature | 25° C.-30° C. |
| (3) Electrolytic tub | Length 125 mm |
| (4) Wire speed | 0.25 m/min–0.47 m/min |
| (5) Total current turned on | 2A |

The shape of wire material thus obtained is shown in FIG. 9.

Example 6

Similarly to Example 5, however, making the feeding speed of wire material constant, the turned-on current was increased gradually as shown in FIG. 8.

The tapered wire material thus obtained was same as one shown in FIG. 9.

As evident from FIG. 9, smooth tapering is given to the tapered wire material obtained by the inventive device.

Moreover, the comparison of electrolytic solutions is as follows:

Example 7

Employing a 1 mmφ Ni-Ti alloy (50.9–49.1 at %) wire material and using a bath comprising 50 vol. % of methanol, 40 vol. % of glycerine and 10 vol. % of perchloric acid, the electrolytic polishing was conducted for 10 minutes at ambient temperature applying a voltage of 25 V.

Example 8

Employing the same wire material and using a bath comprising 30 vol. % of ethanol, 50 vol. % of glycerine and 20 vol. % of perchloric acid, the electrolytic polishing was conducted for 10 minutes at ambient temperature applying a voltage of 25 V.

Example 9

Employing the same wire material and using a bath comprising 8 vol. % perchloric acid-92 vol. % acetic acid, the electrolytic polishing was conducted for 10 minutes at ambient temperature applying a voltage of 25 V.

Comparative example 1

Similarly, the experiment was conducted in a bath of $HF:HNO_3 = 1:4$ (molar ratio).

With respect to above-mentioned Example 7–9 and Comparative example 1, the smell of bath and the surface situation were observed and, in addition, the dissolution rate of wire material was determined, the results of which are put down in Table 1.

TABLE 1

| | Surface Situation | Smell of bath | Dissolution rate |
|---|---|---|---|
| Example 7 | ⊚ | No | 12 μm/min |
| Example 8 | ⊚ | No | 14 μm/min |
| Example 9 | ○ | Yes | 10 μm/min |
| Comparative example 1 | X | Yes | 8 μm/min |

As evident from Table 1, in the examples of the invention, the surface situation was good, no smell of bath was felt except Example 9, and the dissolution rate was also as fast as 12 to 14 μm/min.

Besides, in Example 9, the smell of bath was felt, but the surface situation was good, thus it is possible to use, if investigating from the aspects of installation such as de dorizing device.

On the contrary, in comparative example, the surface situation was not good, bad smell was felt strongly, and the dissolution rate was slow. Utilizability in the industry As described above, in accordance with the invention, the change in wire diameter in the longitudinal direction of wire material can be controlled arbitrarily and the processings such as tapering and joggling can be given efficiently and yet with high precision.

Moreover, for the electrolytic polishing bath of the inventive processing device, if using monovalent alcohol and trivalent alcohol, no bad smell is felt and they are suitable for efficiently obtaining the polished material of Ni-Ti alloy with good surface situation.

We claim:

1. A method of continuously processing wire material, to produce a taper on the wire material comprising:
    passing a long wire material continuously at a speed through an electrolytic polishing bath with a cathode installed therein;
    turning on electricity only when a portion of said wire to be processed passes through said electrolytic polishing bath; and
    increasing the speed when a nonprocessing portion of the wire passes through the electrolytic polishing bath, thereby a taper is produced.

2. The processing method of claim 1, wherein the wire material is a superelastic alloy comprising 50.5 to 53.0 atomic % of Ni and the balance of Ti.

3. The processing method of claim 1, wherein the wire material is a superelastic alloy substituted part of at least one of Ni and Ti in 50.5 to 53.0 atomic % of Ni and 49.5 to 47.0 atomic % of Ti with any one kind or two or more kinds of Cr, Fe, Co, Mo, V, Pd, W and Cu within a range of 0.01 to 5.0 atomic % of each.

4. The processing method of claim 1, wherein the portion of wire material which is processed is tapered or grooved.

5. A method of continuously processing wire material comprising:
   passing a long wire material continuously at a speed through an electrolytic polishing bath with a cathode installed therein;
   turning on electricity only when a portion of said wire to be processed passes through said electrolytic polishing bath; and
   increasing the speed when a nonprocessing portion of the wire passes through the electrolytic polishing bath, thereby a taper is produced; and
   wherein an electrolytic tub comprises therein said electrolytic polishing bath having 10 to 50 vol % of trivalent alcohol, 5 to 20 vol % of perchloric acid and the balance of monovalent alcohol.

6. A method of continuously processing wire material to produce a taper on the wire material comprising:
   passing a long wire material continuously at a speed through an electrolytic polishing bath with a cathode installed therein;
   turning on electricity only when a portion of said wire to be processed passes through said electrolytic polishing bath; and
   increasing the speed when a nonprocessing portion of the wire passes through the electrolytic polishing bath, thereby a taper is produced; and
   wherein an electrolytic tub comprises therein said electrolytic polishing bath having 80 to 95 vol. % of acetic acid and 5 to 20 vol % of perchloric acid.

* * * * *